United States Patent [19]

Murthy et al.

[11] Patent Number: 5,777,221

[45] Date of Patent: Jul. 7, 1998

[54] VOLUME DETECTION APPARATUS AND METHOD

[75] Inventors: Kurukundi Ramesh Murthy, Fairview Park; Ying Cha, N. Olmsted, both of Ohio

[73] Assignee: Chiron Diagnostics Corporation, E. Walpole, Mass.

[21] Appl. No.: 826,330

[22] Filed: Mar. 27, 1997

Related U.S. Application Data

[63] Continuation of Ser. No. 499,820, Jul. 10, 1995, abandoned.

[51] Int. Cl.[6] .................................................. G01F 17/00
[52] U.S. Cl. .............................. 73/149; 73/1.16; 73/861; 250/577
[58] Field of Search ................. 73/149, 861, 864.11, 73/863.01, 863.02, 1.16; 250/577, 573; 356/379

[56] References Cited

U.S. PATENT DOCUMENTS

| | | | |
|---|---|---|---|
| 4,011,459 | 3/1977 | Knollenberg et al. | 73/865.5 |
| 4,366,384 | 12/1982 | Jensen | 250/577 |
| 4,384,578 | 5/1983 | Winkler | 604/114 |
| 4,399,711 | 8/1983 | Klein | 250/577 |
| 4,517,302 | 5/1985 | Saros | 73/864.22 |
| 4,816,695 | 3/1989 | Lavin | 250/573 |
| 4,844,887 | 7/1989 | Galle et al. | 422/65 |
| 4,897,797 | 1/1990 | Free, Jr. et al. | 364/500 |
| 4,931,774 | 6/1990 | Bachman | 250/577 |
| 5,211,626 | 5/1993 | Frank et al. | 604/65 |
| 5,271,902 | 12/1993 | Sakka et al. | 73/863.01 |
| 5,463,228 | 10/1995 | Krause | 250/577 |

FOREIGN PATENT DOCUMENTS

| | | |
|---|---|---|
| 0109198 | 5/1984 | European Pat. Off. |
| 0416808 | 3/1991 | European Pat. Off. |
| 2106670 | 4/1983 | United Kingdom. |

*Primary Examiner*—Hezron E. Williams
*Assistant Examiner*—Nashmiya Fayyaz
*Attorney, Agent, or Firm*—Arthur S. Morgenstern; Charles L. Gagnebin, III; Robert P. Blackburn

[57] ABSTRACT

A failsafe apparatus for verifying a volume of aspirated reagent before it is provided to dilute a sample in an automated assay instrument. A pump draws reagent through a tube having a reagent probe disposed at one end. An optical flow detector includes an optical source disposed proximate the tube to illuminate the interior of the tube, and a photodetector oriented ninety degrees about the circumference of the tube from the source to detect reflected illumination from the contents of the tube. The photodetector provides one voltage level with gas/air within the tube, and a second level with a liquid within the tube. A circuit in communication with the detector discriminates between the two levels. The rate at which aspirate is pumped and the volume of the tube from a probe tip inlet to the detector are known constants. Therefore, a given volume of aspirate takes a predictable amount of time to pass from tip to detector. The actual time is determined by measuring the elapsed time between the start of the aspiration of a reagent, and a liquid-air transition detected at the end of the aspirated reagent. If the liquid-air transition is not seen at the expected time, one of several problems with the system are assumed, and the assay is cancelled.

14 Claims, 4 Drawing Sheets

VOLUME DETECTION APPARATUS AND METHOD

This application is a continuation application under §1.62 of prior application application No. 08/499,820, filed Jul. 10, 1995, now abandoned.

FIELD OF THE INVENTION

The present invention relates to optical flow verification systems, and in particular to an optical flow verification system employing reflectivity measurements to confirm aspiration of a liquid volume.

BACKGROUND OF THE INVENTION

Medical laboratories increasingly rely upon automated assay equipment in order to handle large numbers of assays efficiently in terms of time and cost, and further to increase the reliability of such assays by decreasing the amount of human intervention involved in such assays. However, this reduction in human intervention necessitates a corresponding increase in equipment and devices which ensure the accurate performance of such automated assays. In particular, regulatory agencies responsible for oversight of such testing are reluctant to approve certain forms of automated equipment absent enhanced monitoring and error reporting devices.

Assay equipment currently in use is commonly programmed for withdrawal of a desired reagent in preparation for execution of an assay. While such programmed aspirations are typically accurate, there remains the possibility that a reagent source has run dry though the assay equipment continues to aspirate from the empty reagent container, giving a "short shot" of reagent. Further, while an initial indication that reagent exists in a respective container prior to aspiration may be provided, equipment does not currently detect the evacuation of a supply of reagent during an aspiration. Finally, reagent aspiration equipment in existing automated assay apparatus does not provide the capability to detect an occlusion or an incorrect flow rate in real time or errors from a line break.

Optical verification systems are presently used to measure the transmittance of light through a tube as affected by the contents of the tube. Such transmittance detectors include a light source disposed opposite a light sensor on either side of a tube and are primarily useful for detecting and identifying the contents of a tube at any given moment, and do not find utility in confirming a volume of aspirated liquid.

SUMMARY OF THE INVENTION

The present invention provides an apparatus for verifying a volume of reagent aspirated within an automated assay instrument. A tube has a reagent probe disposed at one end, and a pump or like device disposed at an opposite end. Intermediate the probe and the pump is an optical fluid detector having a housing, through which a transparent portion of the tube passes. Within the fluid detector housing, the fluid detector includes an optical source, such as an infra-red light emitting diode, disposed proximate the tube and oriented to illuminate the interior of the tube. The fluid detector also includes, within the housing and proximate the tube passing therethrough, a photodetector, oriented ninety degrees about the circumference of the tube to detect optical source illumination reflected off an interior surface of the tube opposite the optical source.

The photodetector provides one voltage level when a gas is within the tube in the optical fluid detector, and a different voltage when a liquid is within the tube. This is due to the absolute differences between the refractive indexes of the content of the tube and the tube itself. A threshold determining and comparison circuit in communication with the detector discriminates between the two levels. The rate at which aspirate is pumped and the volume of the tube from a probe tip inlet to the detector are known, typically by using a stepper motor driven syringe plunger on the end of the tube. Therefore, a given volume of aspirate should take a predictable amount of time (or steps) to pass through the detector, taking into consideration established tolerances. Typically, the tube is water filled to the probe tip before aspiration. Time (or stepper motor steps) is measured from the start of the aspiration of reagent. A liquid-air transition is detected at the end of the aspiration of reagent occasioned by the tip being withdrawn from the reagent source and the pump being driven further to place the reagent in a heater zone. If the liquid-air transition is not seen at the expected time, one of several problems with the aspiration are assumed, and the assay is cancelled.

It is an object of the present invention to provide to an automated assay instrument offering an enhanced measure of confidence in the withdrawal accuracy of a desired quantity of aspirate. It is a further object of the present invention to provide error detection and notification which is applicable to a variety of error conditions.

BRIEF DESCRIPTION OF THE DRAWINGS

These and other features of the present invention are more fully set forth below in the fully exemplary detailed description and accompanying drawings of which.

DETAILED DESCRIPTION

Figure 1:
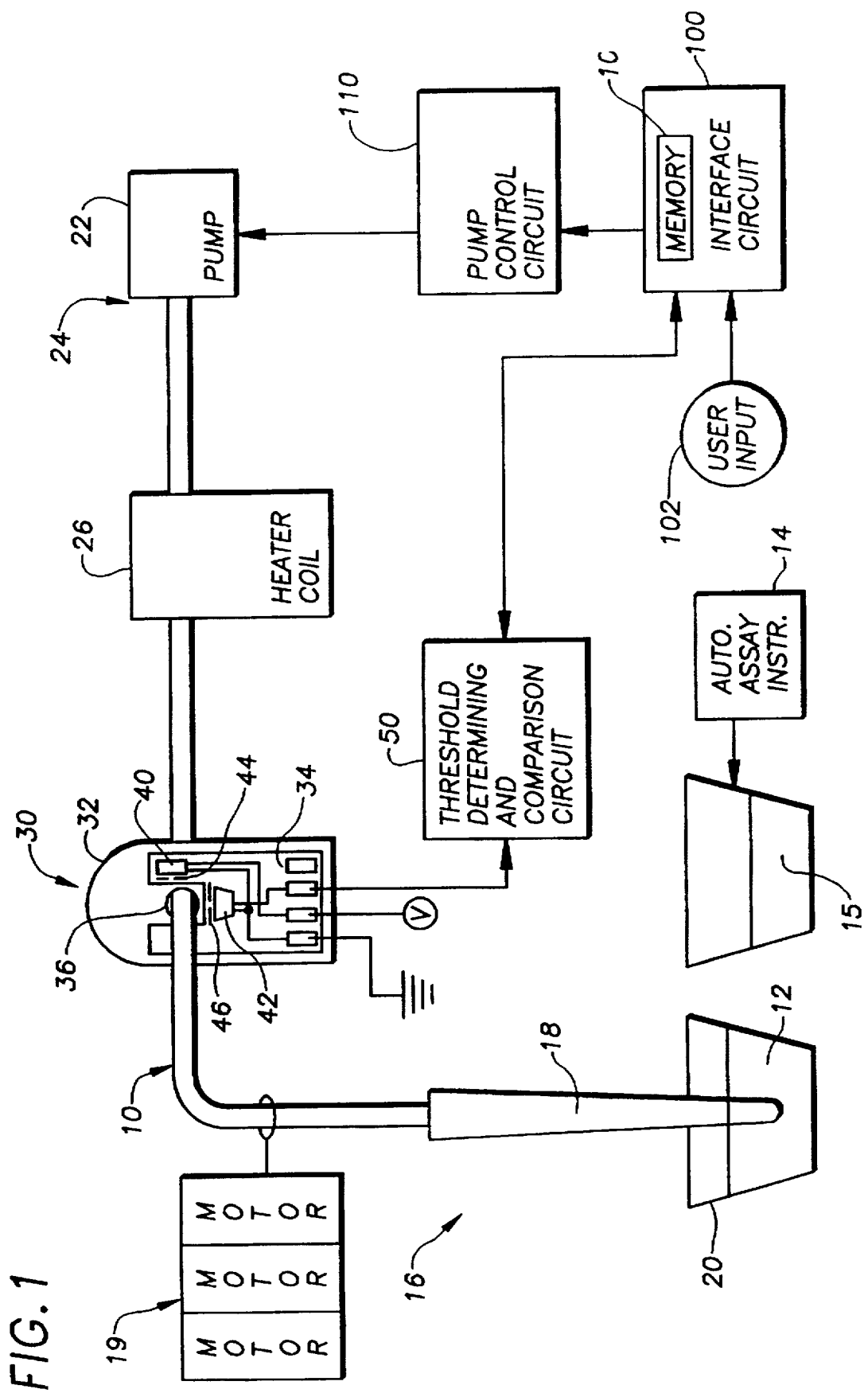
FIG. 1 is a schematic view of elements comprising a volume detection apparatus according to the present invention.

Various components of the volume detection apparatus according to the present invention are illustrated in FIG. 1. In particular, a tube 10 provides aspirate 12 such as a reagent for sample 15 dilution at a station within an automated assay instrument 14 from a reagent container 20. A probe 18 is connected to a first end 16 of the tube 10 for withdrawal of reagent 12 from the container 20 and into the tube 10. In a preferred embodiment, the probe 18 is manipulated automatically by one or more motors 19 such as stepper motors to aspirate from the reagent container 20 and dispense in the sample container 15. These motors translate the probe from one container to another.

To withdraw reagent into the tube, a pump 22 is disposed at a second end 24 of the tube 10. The pump 22 in one embodiment is a positive displacement pump such as a diluter or syringe pump.

Intermediate the tube first and second ends 16, 24, the illustrated embodiment includes a heater coil 26. In some situations, it is preferable to refrigerate reagents to maintain their efficacy. However, this necessitates the heating of the reagent prior to use in the automated assay instrument 14. Otherwise, the lowered temperature of the reagent may adversely affect the performance of an assay in which it is used.

Also disposed intermediate the first and second ends 16, 24 of the tube 10 is an optical fluid detector 30 having a housing 32. The tube 10 passes through an orifice 36 in the housing 32 so that the tube 10 is generally normal to a plane defined by the housing 32. For the purposes of illustration, a cover of the housing 32 has been removed. A circuit board 34 disposed within the housing 32 provides a mounting surface for an optical source 40 and a photodetector 42 disposed adjacent the tube 10.

In a first embodiment, the optical source 40 is a light emitting diode (LED) generating infrared illumination. In a further embodiment, the optical source 40 is fabricated directly on the circuit board 34 as an integrated device. Power and ground leads are further provided on the circuit board 34 in communication with the optical source 40.

The optical source 40 is provided with a narrow width slit aperture 44, parallel to the tube 10. This aperture 44 allows IR illumination to enter the tube 10 in a narrow dispersion pattern. Preferably, the housing 32 and associated tube 10 support elements integral to the housing 32 and adjacent to the optical source 40 and photodetector 42 are formed of a material opaque to visible light, but transparent to IR illumination. This avoids spurious readings due to ambient illumination entering the photodetector 42.

The photodetector 42 is similarly disposed on the circuit card 34 adjacent the tube 10, though the photodetector 42 is located ninety degrees about the circumference of the tube 10 from the optical source 40. Similar to the optical source 40, the photodetector 42 is provided with a small width slit aperture. Thus, the photodetector 42 is particularly sensitive to IR light reflected off the interior wall of the tube 10, which varies with the reflective index of the contents of the tube 10. The photodetector 42 is therefore provided as a reflectivity sensor as contrasted with a turbidity sensor which detects light scattered by the contents of the tube 10.

In summary, light from the optical source 40 illuminates the interior of the tube 10. A portion of this light is reflected off an inner wall of the tube 10 to a degree determined by the respective reflective indexes of the tube and the contents of the tube and is detected by the photodetector 42. The photodetector 42 detects a smaller amount of reflected light when there is liquid within the tube 10 in front of the optical source 40 and photodetector 42 as compared to when a gas such as ambient air is within the tube 10. The respective apertures 44, 46 enhance the sensitivity of the apparatus such that air bubbles of a few microliters are detectable.

The photodetector 42 of the present invention is interfaced to a circuit 50 labelled "Threshold Determining and Comparison Circuit". This circuit, which is illustrated in detail in FIG. 2, establishes a reference voltage level against which signals from the photodetector 42 are compared to establish when liquid versus air is within the tube adjacent the photodetector 42.

Figure 2:
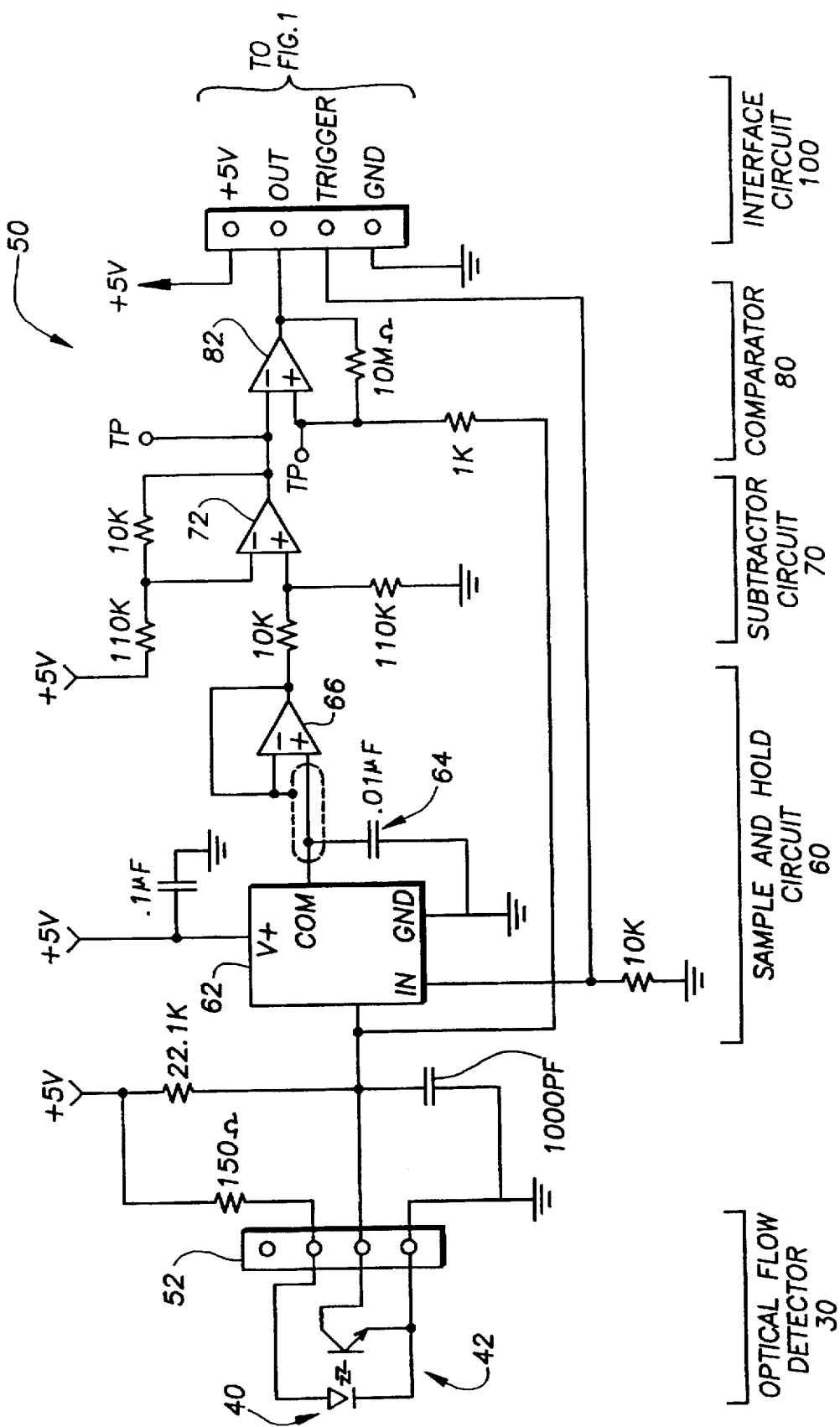
FIG. 2 is a schematic view of a threshold determining and comparison circuit as employed in the apparatus of FIG. 1.

With reference now to FIG. 2, the threshold determining and comparison circuit 50 includes a connection interface 52 to the optical fluid detector 30. Power and a ground reference are provided to the fluid detector 30. A signal from the photodetector 42, representative of the quantity of light reflected to the photodetector 42, is provided to a sample and hold circuit 60. Included within this circuit 60 is an analog switch 62, in one embodiment a "MAX323CSA" manufactured by Maxim Integrated Products of Sunnyvale, Calif., USA. The switch 62 is utilized by connecting the photodetector 42 output to a normally open (NO) input terminal of the switch 62. A trigger signal, provided from an interface circuit 100 (to be described subsequently), is connected to a logic input (IN) terminal of switch 62 to control the operation of the switch 62. In one logic state, the photodetector output is connected through the normally open terminal to a common terminal (COM). In another state, the photodetector 42 signal is disconnected from the COM output while its last value is held by capacitor 64. This results in the sample and hold circuit 60 latching onto a voltage level coming from the photodetector 42. The op-amp 66 receives this signal as a buffer amp for preventing leakage of the sample and hold output.

The output of the buffer 66 is provided to a subtractor circuit 70 which includes an op-amp 72 configured to subtract 0.45 V from the output of the sample and hold circuit 60 and to provide the result as a reference voltage ($V_{ref}$).

Finally, the threshold determining and comparison circuit 50 includes a comparator 80 including an op-amp 82 configured to compare the output from the photodetector 42 with the reference voltage from the subtractor circuit op-amp 72. The result is then provided as an output from the threshold determining and comparison circuit 50 and as an input to the interface circuit 100.

With reference to FIG. 1, the interface circuit 100 receives user input from a source 102, including the expected volume of reagent to be aspirated. The interface circuit 100 further comprises a memory 104 for storing information such as the known volume of the probe 18 with the tube 10 up to the optical fluid detector 30, as well as the rate at which the pump 22 withdraws reagent into the probe 18 and tube 10. With volume and rate known, the expected time for a reagent aspiration to pass by the detector 30 is calculated. Output from the threshold determining and comparison circuit 50 is checked (as described later) to verify that the aspiration indeed takes the expected amount of time within some tolerance. If not, a malfunction in the aspirate withdrawal system is indicated and the system can react accordingly, as by the cancellation of further reagent aspirations, the notification of a user of the error condition, and the initiation of diagnostic measures.

The interface circuit 100 also provides commands to a pump control circuit 110 based upon the user input from source 102. Such input in one embodiment includes pump on and off signals in the form of a command to begin an assay. In an alternative embodiment, such input includes pump rate information. In the latter embodiment, the variable rate is factored into the elapsed time calculations carried out by the interface circuit 100.

The generation of various signals from the photodetector 42 output and their use in the threshold determining and comparison and interface circuits 50, 100 are now described with reference to FIGS. 3 through 5. Here, only the tube 10, the probe 18, the optical fluid detector 30 (with a cover attached), and the reagent container 20 are carried over from FIG. 1 for the sake of simplicity. As previously noted, the interface circuit 100 has stored therein the known volume of the probe 18 and tube 10 from a distal end of the probe 18 to the optical fluid detector 30, as well as the rate at which the pump 22 draws air and liquid through the tube 10. Therefore, the elapsed time required to aspirate a certain volume of reagent through the probe 18 and tube 10 to the fluid detector 30 can be calculated.

The presently disclosed invention provides an indication of the actual elapsed time in the following manner. The presently disclosed apparatus is a water-backed system, meaning that the probe 18 and tube 10 are filled with water up to a region, for example, 28 when not conveying reagent or air. In a first embodiment, water is provided by automatically manipulating the probe 18 into a water-filled container 120 and activating the pump 22, thus drawing water 28 into the probe 18 and tube 10. In a second embodiment, water is provided within the tube 10 by operation of one or more valves connecting the tube 10 to another water-filled container (not illustrated).

Figure 6:
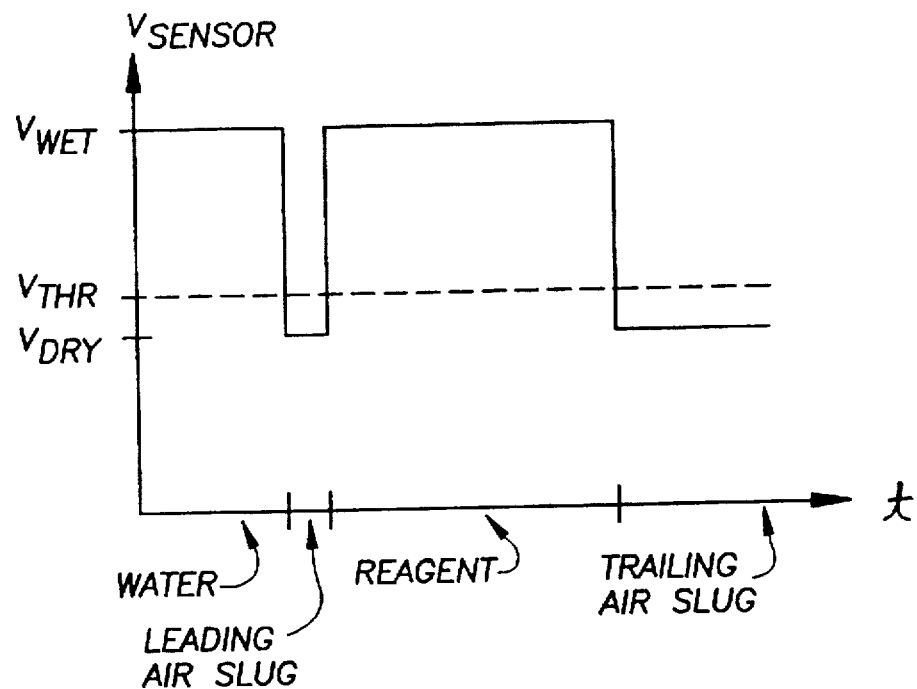
FIG. 6 is a graph illustrating the relative amplitude and timing of signals employed in the detection apparatus of FIG. 1.

Light is less readily reflected within the tube 10 when it is filled with a liquid. Therefore, a higher voltage level ($V_{wet}$) is returned by the photodetector 42 to the sample and hold circuit 60 when liquid is in the tube 10 than when air is within the tube 10 ($V_{dry}$), as illustrated in FIG. 6. With water throughout the tube 10, and in particular within the optical fluid detector 30, the interface circuit sends a trigger signal to the threshold determining and comparison circuit 50. As previously noted with respect to FIG. 2, the trigger signal causes the sample and hold circuit 60 to hold the current voltage level ($V_{photo}$) from the photodetector 42. This level is then subject to the subtractor circuit 70.

The goal is to compare a returned voltage from the photodetector 42 ($V_{photo}$) to a reference voltage ($V_{ref}$) in order to determine whether air or liquid is before the photodetector 42 at that moment. To make the present optical fluid detector 42 independent of the unique characteristics of each particular optical fluid detector 30 ($V_{wet}$ and $V_{dry}$ may not be the same for each detector), a threshold level is chosen slightly above the maximum returned voltage level when air is within the tube at the photodetector 42 ($V_{dry}$).

Since the difference between wet ($V_{wet}$) and dry ($V_{dry}$) voltages does not fall below 0.5 V in any optical fluid detector 30, regardless of absolute values, the voltage threshold ($V_{thr}$) (above which is always $V_{wet}$ and below which is always $V_{dry}$) is chosen as $V_{dry}$ minus a value slightly less than the difference between $V_{wet}$ and $V_{dry}$. In one embodiment, $V_{wet}-V_{dry} \approx 0.5$ V, so $V_{thr}$ is chosen as $V_{wet}-0.45$ V. As such, the subtractor circuit 70 in this instance subtracts 0.45 V from $V_{wet}$ to form $V_{thr}$, $V_{wet}$ being determined by triggering the sample and hold circuit 60 when water is within the tube 10 at the optical fluid detector, such as immediately before the start of aspirating a reagent sample. Since $V_{wet} > V_{thr}$, the output of the comparator ($V_{out}$) 80 is "high". The threshold level relative to the absolute values of the photodetector is shown in FIG. 6. By relying upon a guaranteed minimum difference between $V_{wet}$ and $V_{dry}$ rather than on the absolute values of these measurements, the need to calibrate is eliminated.

Next, to provide an indication that a reagent volume is about to pass by the detector 30 within the tube, the probe 18 is withdrawn from all containers and the pump is activated for a relatively short period of time prior to withdrawing a quantity of reagent 12 into the tube 10. This causes a leading air slug 122 to be drawn into the probe 18 (FIGS. 3 and 4). However, the photodetector 42 will continue to sense liquid in the tube until the leading air slug 122 progresses through the tube 10 to the optical fluid detector 30.

Figure 4:
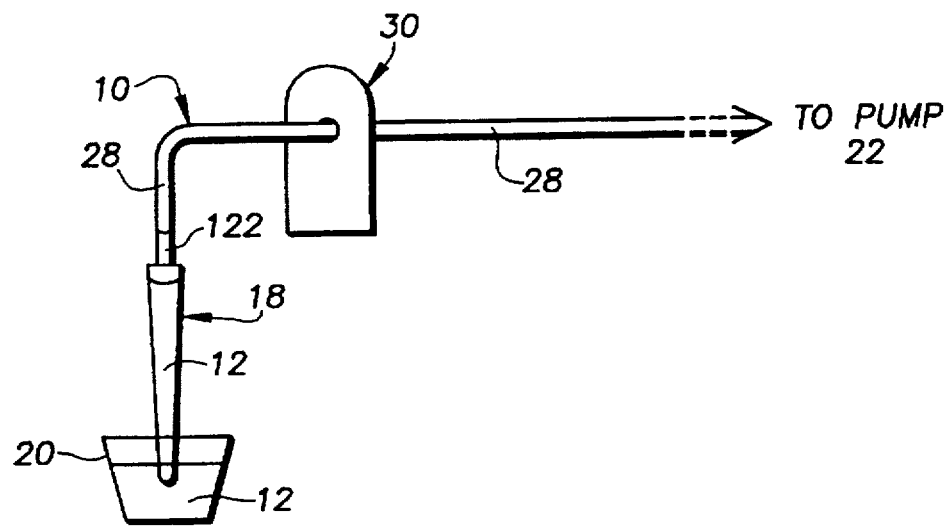

Next, as shown in FIG. 4, the probe 18 is manipulated into the reagent container 20 and the pump 22 is activated by the pump control circuit 110. Feedback circuitry (not illustrated) may be provided in a further embodiment in order to verify the physical disposition of the probe 18 within the reagent container 20. At this point, water remains in the majority of the fluid path, followed by the leading air slug 122 which is shown just emerging above the probe 18.

Figure 5:
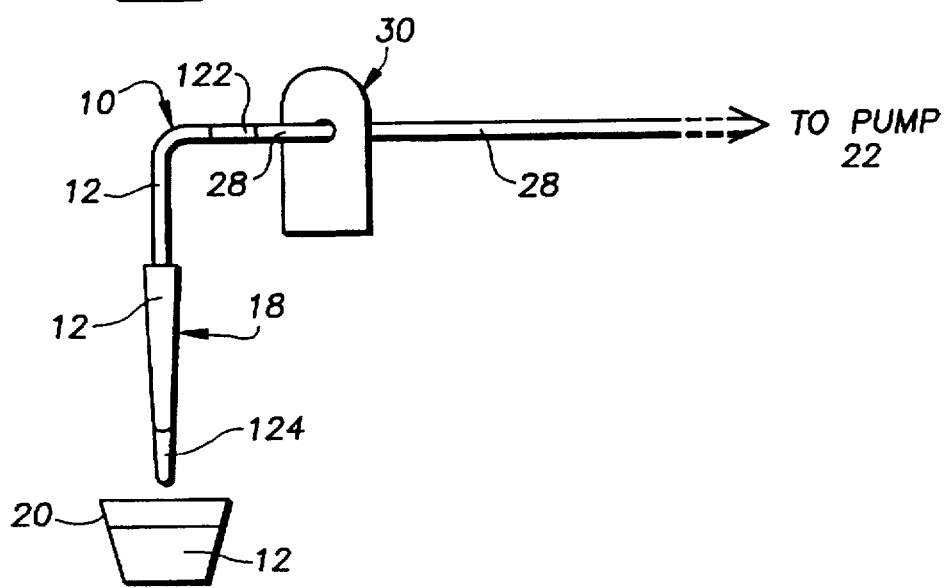
Figure 7:
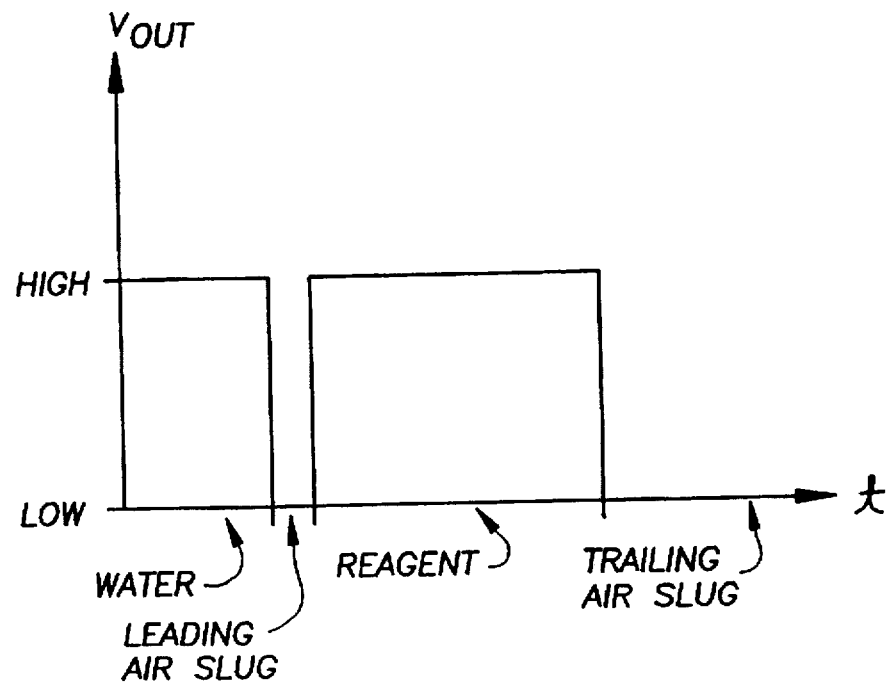
FIG. 7 is a graph illustrating the timing of signals employed in the detection apparatus of FIG. 1.

In FIG. 5, a quantity of reagent 12 has been withdrawn into the probe 18 and tube 10, and the probe 18 has been raised out of the reagent container 20. The pump 22 then draws a trailing air slug 124 into the probe 18 following the reagent 12 aspirate. As shown, the optical fluid detector 30 is typically, but not necessarily, still presented with water in the tube 10, and as such the photodetector voltage remains at $V_{wet}$ and the output of the comparator 80 ($V_{out}$) remains "high" as in FIG. 7.

Further activation of the pump 22 causes the leading air slug 122 to progress until it is at the optical source 40 and photodetector 42. At this point, the higher reflectivity of air is sensed by the photodetector 42, resulting in a "low" output ($V_{out}$) of the comparator circuit 80, as in FIG. 7. Firmware within the interface circuit 100 checks to see if $V_{out}$ remains "low" for a minimum period, corresponding to a minimum leading air slug 122 volume within the tube 10. If large enough, the firmware assumes this is the leading air slug 122 and begins counting on the next "low" to "high" transition of $V_{out}$ which corresponds to the detection of liquid (reagent) passing through the tube 10 before the photodetector 42.

If the air detected before the photodetector does not persist long enough (i.e. $V_{out}$="low" for too short a time), it is assumed that this air was an air bubble and not the leading air slug 122.

Once the leading air slug 122 has been identified, the interface circuit continues counting until a "high" to "low" transition is returned from the threshold determining and comparison circuit 50, corresponding to the passage of the trailing air interface 124 before the photodetector 42. The interface circuit 100 is provided with the desired reagent volume via the user interface 102 or via its own memory 104. In conjunction with known rate and volume information, the interface circuit 100 is capable of calculating the time in which the trailing air slug 124 should have been seen, within a given target range. The larger the removed volume, the larger the target range. The probe is then manipulated by motors 19 to a point where the reagent can be dispensed in a sample 15, or is conveyed within a system of valves and further tubes (not illustrated).

If the trailing air interface 124 is not seen within this range, the interface circuit 100 sends an indication of this state for use, for example, in halting all further assays using this reagent in particular or all reagents, and/or of notifying a user via a user interface. This error could occur due to a number of causes, including an empty reagent container 20, an occluded tube 10 or probe 18, and a failing or failed pump 22.

Figure 3:
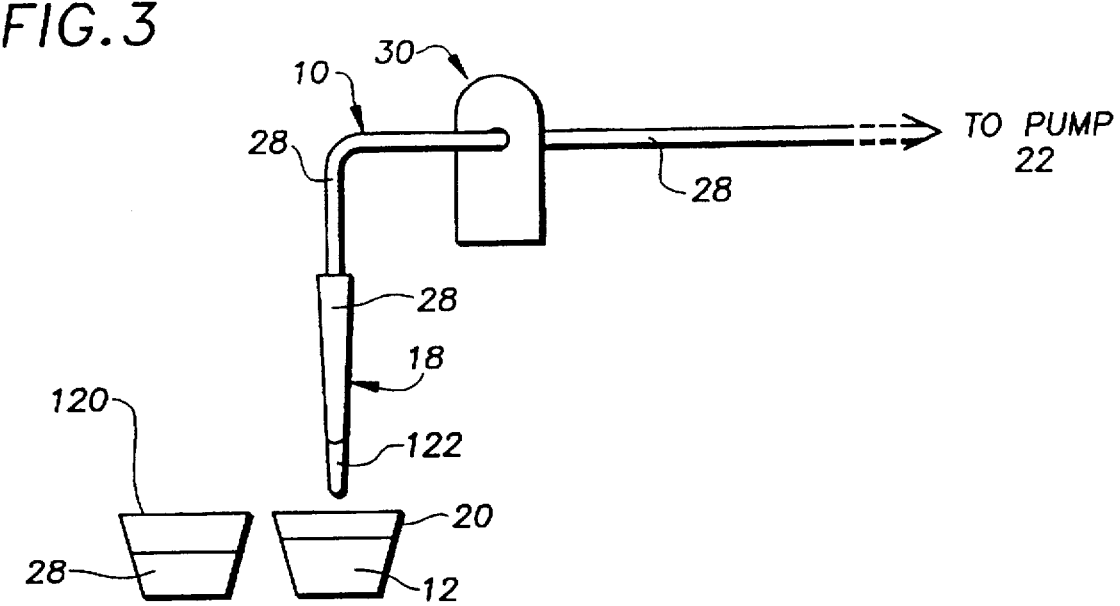
FIGS. 3 through 5 are simplified illustrations of the detection apparatus of FIG. 1 in various stages of aspirating a reagent sample.

In FIGS. 3 through 5, the volume of reagent aspirated was small enough so that both the leading and trailing air regions 122, 124 were within the tube 10 or probe 16 before the leading air slug 122 was within the optical fluid detector 30. In other instances, the leading air slug 122 is drawn within the optical fluid detector 30 while the probe 18 is still within the reagent container 20 and while the pump is still drawing reagent into the probe 18 and tube 10. This does not impact the ability of the threshold determining and comparison circuit 50 or the ability of the interface circuit 100 to count as the reagent 12 is drawn through the apparatus.

Having described preferred embodiments of the invention, it will now become apparent to one skilled in the art that other embodiments incorporating the concepts may be used.

Though the invention has been described as finding utility as part of an automated assay instrument requiring reagent, the presently disclosed invention can be utilized for the transfer of other liquids for other purposes.

Further, though a positive displacement pump such as a diluter is disclosed, other pumping devices can be used with the present invention such as dilutors. In fact, this verification system is particularly useful with pumps which are not as reliable in terms of accuracy of withdrawn liquid.

The tube of the present invention is formed of Teflon (E. I. du Pont de Nemours & Co., Inc., Wilmington, Del., USA), though other non-reactive, light transmissive materials can be used. The choice of frequency for the optical source 40 can also be varied depending upon the tube material and the contents to be sensed.

These and other examples of the invention illustrated above are intended by way of example and the actual scope of the invention is to be determined from the following claims.

What is claimed is:

1. A detector apparatus for measuring a liquid volume aspirated within a tube by a pump, the apparatus comprising:
   a housing having an aperture for passage of said tube therethrough;
   an optical source within said housing and proximate said tube;
   a photodetector within said housing, proximate said tube, and disposed approximately ninety degrees about a circumference of said tube from said source, wherein said photodetector detects changes in light reflection due to tube contents; and
   a volume measuring circuit for detecting the volume of a liquid drawn into said tube by said pump as a function of a temporal point of detection of an air to liquid boundary and a liquid to air boundary, each causing changes in light reflection within said tube and detected by said photodetector, wherein a first time is logged by said volume measuring circuit when said photodetector detects a first change in light reflection within said tube, a second time is logged by said volume measuring circuit when said photodetector detects a second change in light reflection within said tube, and the liquid volume aspirated is determined by said volume measuring circuit using said first and second times and known tube volume and aspiration rate information.

2. The apparatus according to claim 1, wherein said photodetector is calibrated to a water header within said tube.

3. The apparatus according to claim 2, wherein said photodetector detects said changes in light reflection as an increase in light reflection due to a leading air gap, a decrease in light reflection due to said aspirated liquid volume, and an increase in light reflection due to a trailing air gap.

4. The apparatus according to claim 1, further comprising a threshold determining and comparison circuit in communication with said photodetector for differentiating between said change in light reflection due to said air to liquid boundary within said tube and said change in light reflection due to said liquid to air boundary within said tube.

5. The apparatus according to claim 1, further including a control circuit for controlling said pump to aspirate said liquid through said tube at the aspiration rate.

6. The apparatus according to claim 1, wherein said optical source is a light-emitting diode.

7. The apparatus according to claim 1, wherein said tube comprises Teflon.

8. The apparatus according to claim 1, further comprising a probe connected to a first end of said tube for aspiration of said liquid volume through a probe tip.

9. The apparatus according to claim 1, further comprising a liquid heater connected to an end of said tube for heating said aspirated liquid volume at a point beyond said housing.

10. The apparatus according to claim 1, further comprising an optical source slit aperture intermediate said optical source and said tube for defining a narrowly dispersed pattern of illumination within said tube.

11. The apparatus according to claim 1, further comprising a photodetector slit aperture intermediate said photodetector and said tube for limiting illumination received by said photodetector to a narrow band of illumination reflected from an interior wall of said tube.

12. A method for determining a liquid volume aspirated within a tube using an optical fluid detector comprising an optical source disposed adjacent said tube and a photodetector disposed adjacent said tube and rotated approximately ninety degrees about said tube from said optical source, said method comprising the steps of:
   providing an optical signal from said optical source;
   aspirating water within said tube;
   sensing a voltage at said photodetector with water in said tube;
   aspirating a first volume of air within said tube;
   aspirating said liquid volume within said tube;
   aspirating a second volume of air within said tube;
   sensing a first change in voltage from said photodetector as said first volume of air passes by said photodetector, said first change in voltage having a duration greater than a predetermined minimum time;
   sensing a second change in voltage from said photodetector as said liquid volume passes by said photodetector;
   logging a first count from a counter when said second change in voltage is sensed;
   sensing a third change in voltage from said photodetector as the second volume of air passes by said photodetector, said third change in voltage having a duration greater than the predetermined minimum time;
   logging a second count from said counter when said third change in voltage is sensed;
   determining a time interval elapsed between the first count of said counter and the second count of said counter; and
   determining said liquid volume aspirated using said elapsed time interval and known tube volume and aspiration rate information.

13. The method according to claim 12, wherein said step of sensing a first voltage change as said first volume of air passes by said photodetector occurs before said step of aspirating said second volume of air.

14. A method for measuring a liquid volume aspirated within a tube by a pump, comprising:
   aspirating a quantity of water into said tube by said pump;
   establishing a voltage threshold within a comparison circuit based upon light reflection data received from an optical fluid detector proximate said tube;
   aspirating a first volume of air into said tube by said pump;

aspirating said liquid volume into said tube by said pump;

aspirating a second volume of air into said tube by said pump;

detecting said first volume of air in said tube using said detector when an output of said detector falls below said threshold;

detecting said liquid volume in said tube using said detector and starting a counter when said output of said detector rises above said threshold;

detecting said second volume of air in said tube using said detector and stopping said counter when said output of said detector again falls below said threshold, and verifying an output count of said counter against a predetermined count, said predetermined count based upon known tube volume and aspiration rate information in order to provide a measure of the liquid volume aspirated.

* * * * *